(12) United States Patent
Classen et al.

(10) Patent No.: US 7,337,004 B2
(45) Date of Patent: Feb. 26, 2008

(54) METHOD AND APPARATUS FOR VETERINARY RF PAIN MANAGEMENT

(76) Inventors: Ashley M. Classen, 4039 Keller Haslet Rd., Keller, TX (US) 76248; Mark Revenaugh, 23635 S. Molalla Ave., Oregon City, OR (US) 97045

( * ) Notice: Subject to any disclaimer, the term of this patent is extended or adjusted under 35 U.S.C. 154(b) by 475 days.

(21) Appl. No.: 10/774,742

(22) Filed: Feb. 9, 2004

(65) Prior Publication Data

US 2005/0177202 A1 Aug. 11, 2005

(51) Int. Cl.
*A61N 1/34* (2006.01)
(52) U.S. Cl. ............................................ 607/46; 607/3
(58) Field of Classification Search ................ 607/1–2, 607/46, 115, 145, 149, 150, 154, 156, 3; 600/372, 382
See application file for complete search history.

(56) References Cited

U.S. PATENT DOCUMENTS

| | | | | |
|---|---|---|---|---|
| 4,541,432 A | | 9/1985 | Molina-Negro et al. .... 128/421 |
| 5,052,391 A | * | 10/1991 | Silberstone et al. .......... 607/46 |
| 5,976,110 A | * | 11/1999 | Greengrass et al. ........ 604/158 |
| 6,010,467 A | * | 1/2000 | Smith .......................... 601/15 |
| 6,445,955 B1 | | 9/2002 | Michelson et al. ........... 607/46 |
| 6,505,075 B1 | * | 1/2003 | Weiner ......................... 607/46 |
| 6,535,767 B1 | | 3/2003 | Kronberg ...................... 607/72 |
| 6,896,675 B2 | * | 5/2005 | Leung et al. .................. 606/49 |
| 6,918,908 B2 | * | 7/2005 | Bonner et al. ................ 606/41 |
| 7,069,083 B2 | * | 6/2006 | Finch et al. .................. 607/46 |

* cited by examiner

*Primary Examiner*—Carl Layno
(74) *Attorney, Agent, or Firm*—Whitaker, Chalk, Swindle & Sawyer, LLP; Stephen S. Mosher

(57) ABSTRACT

A method and apparatus for reducing chronic pain in animals by radio frequency (RF) neuromodulation of peripheral nerves of the animal is disclosed. The method, using the disclosed apparatus, comprises the steps of attaching active and dispersive percutaneous probes at respective active and dispersive locations relative to a peripheral nerve of the patient associated with the pain to be reduced; generating a first pulsed RF signal for coupling to the active and dispersive probes to verify the location of the peripheral nerve; and generating a second pulsed RF signal for coupling to the active and dispersive probes to modify propagation of pain sensation in the peripheral nerve without ablation thereof. In one embodiment of the apparatus, the active percutaneous probe includes an RF cannula having a conductive spatulate blade conformably attached to a dorsal side of a curved, blunt-ended tubular tip portion of the RF cannula. In another embodiment of the apparatus, a dispersive percutaneous probe includes a pair of 22 gauge needles connected to ground return conductors. In yet another embodiment of the apparatus, a pulsed RF generator is modified to provide specific outputs adapted to the neuromodulation of peripheral nerves in veterinary patients.

61 Claims, 7 Drawing Sheets

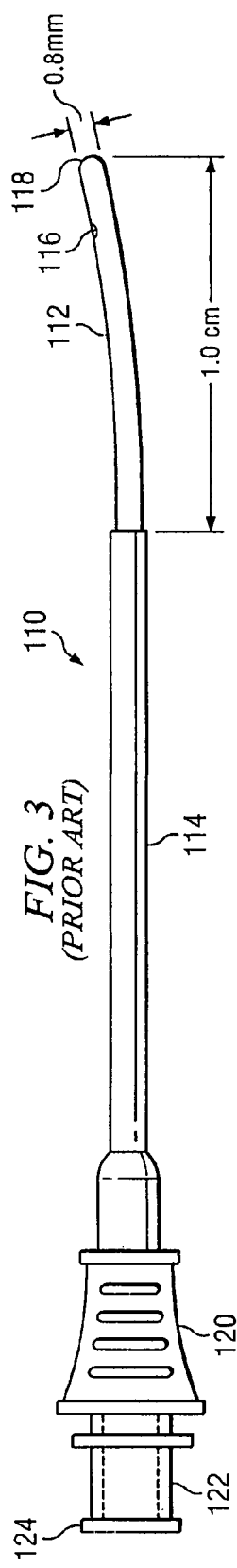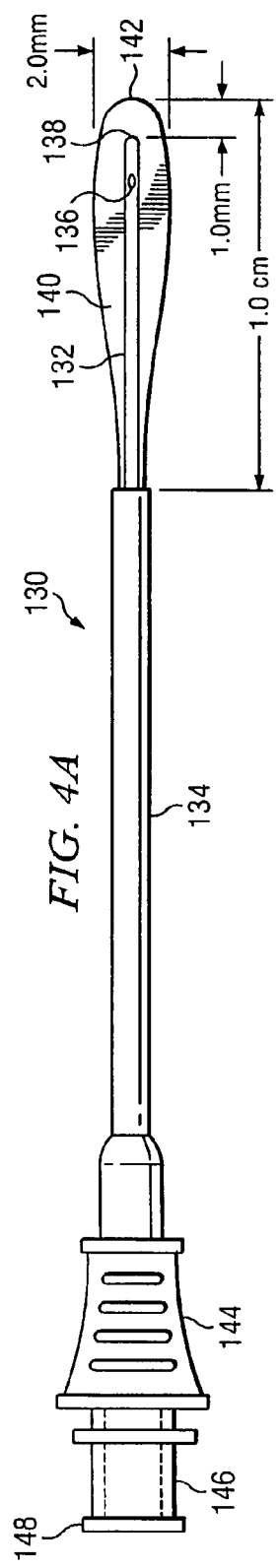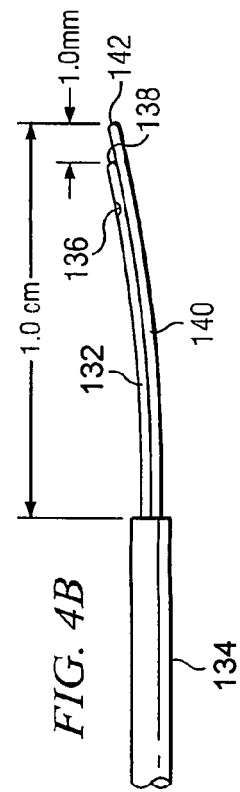
FIG. 3 (PRIOR ART)
FIG. 4A
FIG. 4B

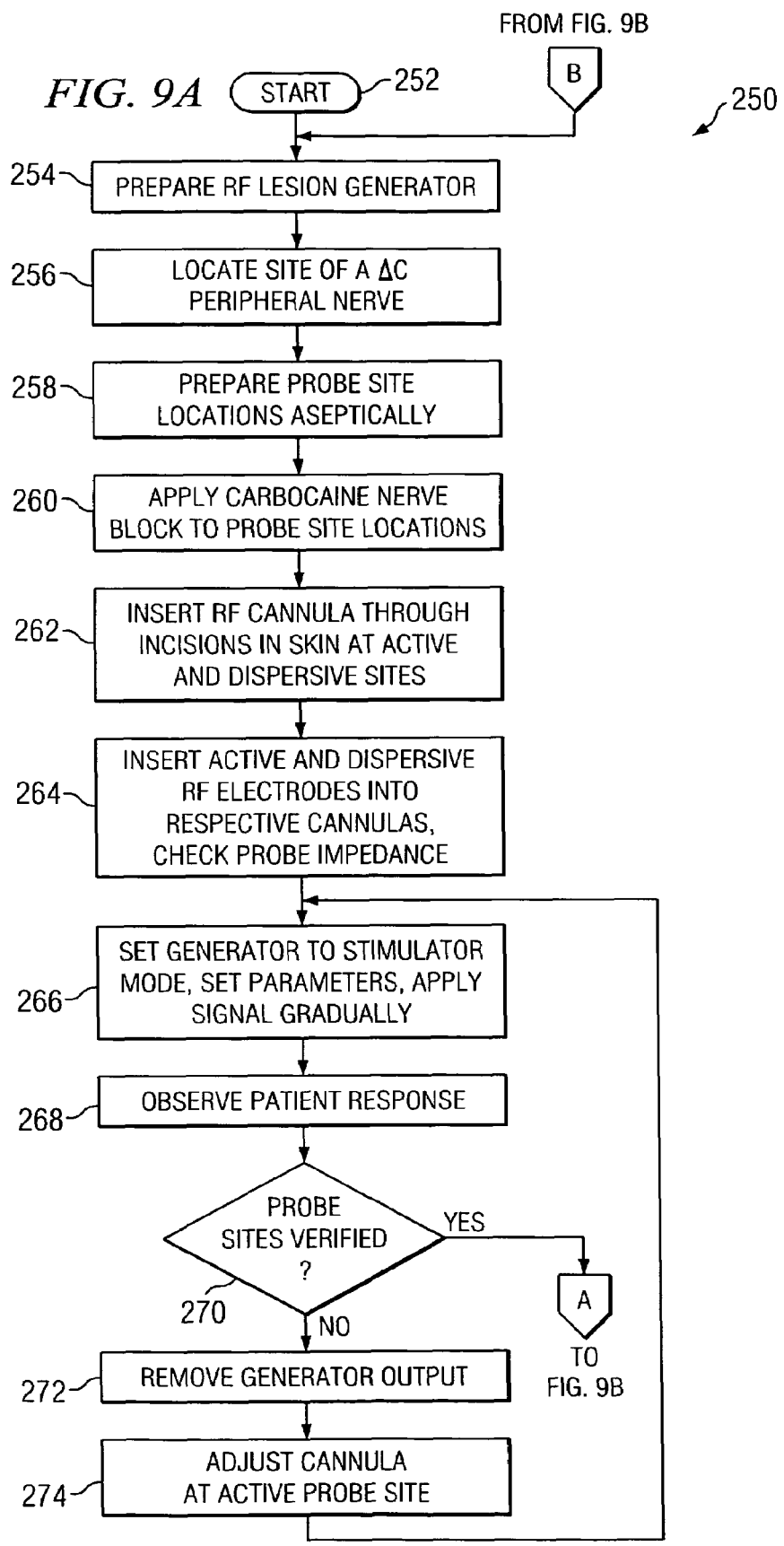

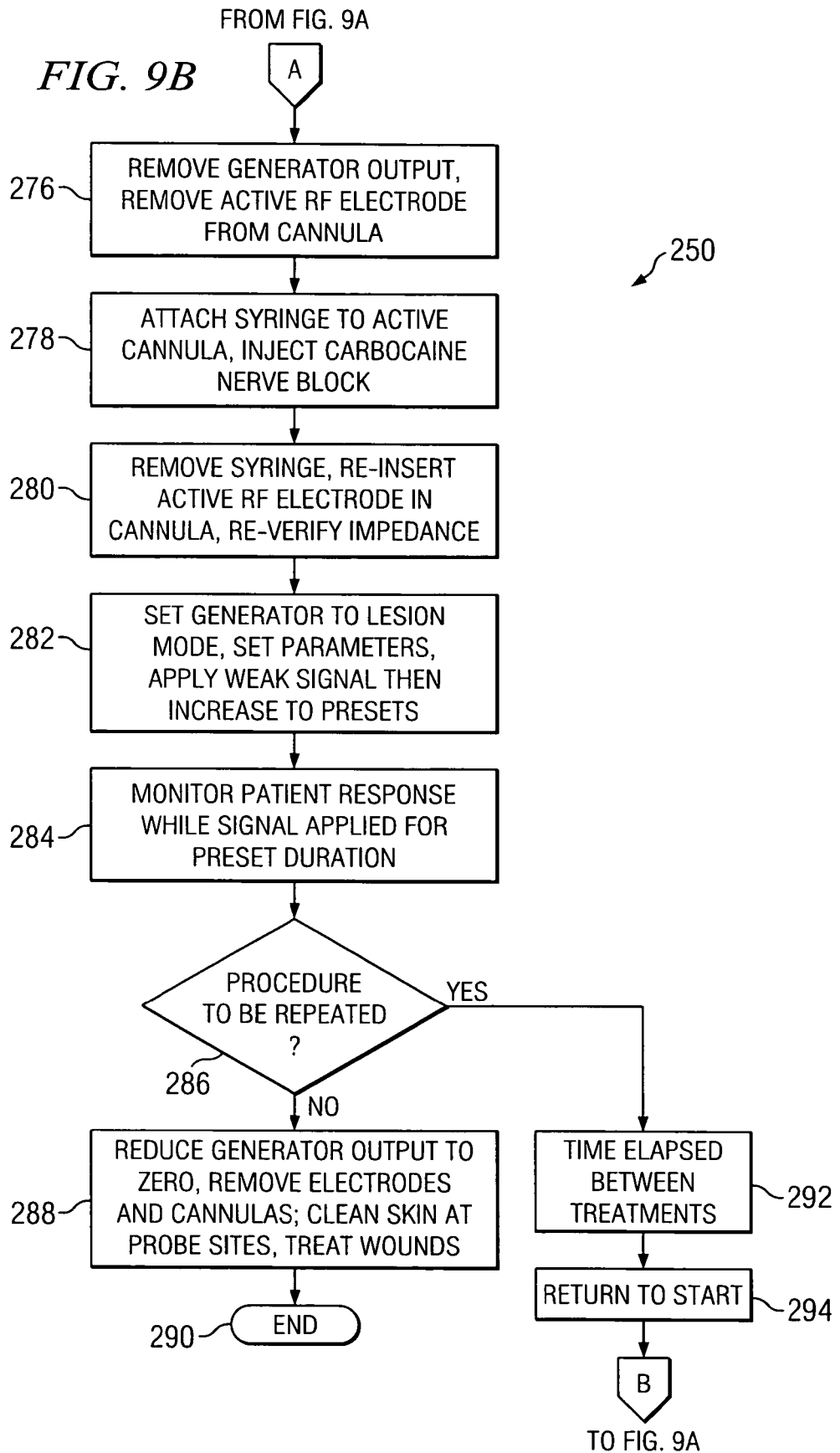

METHOD AND APPARATUS FOR VETERINARY RF PAIN MANAGEMENT

BACKGROUND OF THE INVENTION

1. Field of the Invention

The present invention generally relates to relief of pain in animals using radio frequency electrical signals and, more particularly, to a method and apparatus for equine pain therapy using RF stimulation and lesioning techniques.

2. Description of the Prior Art

The management of pain in animals, particularly large animals such as horses, of the family equinadae, has traditionally relied on rehabilitation strategies, pharmacological intervention and the like. Though often effective, such therapies require significant amounts of time during which to recover from the injury or illness that caused the pain. Further, progress in such therapies may be limited by the presence of the pain during exercises or by the affects of the drugs administered to alleviate the pain while attempting to resume normal function. Moreover, for animals such as horses, that participate in competitive events, drug therapies are often impractical because of rules for drug testing that preclude the use of drugs in the management of pain. Another disadvantage of drug therapies is that the effects are short-lived, lasting only as long as the drug is administered. Further, prolonged reliance on drugs can result in an accumulating resistance to the affects of the particular drug and/or a dependency or difficulties in weaning the patient of continued treatment with the particular drug. Thus, there is a need to provide effective long-term management of chronic pain in animals with minimal significant pharmacological intervention.

The use of pulsed radio frequency (PRF) stimulation—i.e., neuromodulation of peripheral nerves—for medical purposes is not new. In humans, PRF has been described as a therapy for transiently deactivating ADC peripheral nerve fibers. The ADC peripheral nerve fibers are exclusively responsible for chronic pain, while leaving nerve fibers for neuromuscular, acute pain, proprioception (sensory reception of stimuli in muscles, tendons and joints), etc. intact. In general, after the site on the patient's skin is located, aseptically cleansed and desensitized, the peripheral nerve is accessed percutaneously, i.e., through the skin, via a small incision in the skin. The PRF probe is introduced through the incision and applied directly onto the selected peripheral nerve. The PRF energy is regulated as to amplitude, pulse repetition rate and time duration. Also monitored are the impedance of the probe/patient connections and the temperature of the tissues at the probe tips.

However, the use of PRF for pain management in veterinary medicine has not been described heretofore. Several problems must be overcome. One is, while the peripheral nervous systems of animals in principal is very similar to that of humans, the anatomy of animals differs significantly and requires the development of techniques adapted to these anatomical differences. Further, the RF energy parameters that are effective for the treatment of chronic pain in animals are not necessarily the same as used in human PRF therapies. Another is that animals are generally covered with hair, which requires shaving, removal of the natural oils on the skin and antiseptically preparing the skin. This is typically a cumbersome procedure and leaves a bare, unsightly patch of skin until the hair grows back to its previous condition. Moreover, the PRF probes currently available are not well-suited for use with most animals because of size variations and the need for providing a reliable electrical connection to the nerve tissue of animals. Thus, there is a need for PRF apparatus and methods adapted for use in treating chronic pain in animals, as described herein below.

SUMMARY OF THE INVENTION

There is disclosed a method of reducing chronic pain in animals by radio frequency (RF) neuromodulation of peripheral nerves of the animal, comprising the steps of attaching active and dispersive percutaneous probes at respective active and dispersive locations relative to a peripheral nerve of the patient associated with the pain to be reduced; generating a first pulsed RF signal configured according to a first protocol for coupling to the active and dispersive probes via conductive leads, to verify the location of the peripheral nerve; and generating a second pulsed RF signal configured according to a second protocol for coupling to the active and dispersive probes via the conductive leads after the first pulsed RF signal is withdrawn, to modify propagation of pain sensation in the peripheral nerve without ablation thereof, wherein at least the active percutaneous probe includes an RF cannula having a conductive spatulate blade conformably attached to a dorsal side of a curved, blunt-ended tubular tip portion of the RF cannula.

In another aspect there is disclosed an apparatus for reducing chronic pain in animals by radio frequency (RF) neuromodulation of a peripheral nerve of the animal, comprising a generator, for generating pulsed RF signals in at least a first mode and a second mode to be coupled via respective active and dispersive probes to respective active and dispersive locations on an animal patient's body, for reducing chronic pain experienced by the animal without ablation of the peripheral nerve, a set of RF percutaneous probes including at least an active electrode and a dispersive electrode attached to the respective active and dispersive locations on the animal's body, at least the active probe further comprising an RF cannula having a conductive spatulate blade conformably attached along a longitudinal axis to a dorsal side of a curved, blunt-ended tubular tip portion of the RF cannula, and means adapted to connect with the active probe for administering a liquid substance into the tissue of the animal that is in the active location.

In another aspect there is disclosed a radio frequency (RF) cannula, comprising an insulated tubular body for receiving an RF electrode therethrough, a hub at a first end of the tubular body for interfacing with the RF electrode upon its insertion into the tubular body; and a blunt-ended and conductive tubular tip extending from a second end of the insulated tubular body, arcuate approximately along a longitudinal axis of the tubular body and including a conductive spatulate blade having an oval-shaped distal end and conformably attached to a dorsal side of the blunt-ended, conductive and arcuate tubular tip.

BRIEF DESCRIPTION OF THE DRAWINGS

FIG. 3 illustrates a prior art RF cannula;

FIG. 4A illustrates a plan view of one embodiment of an RF cannula modified according to the present invention;

FIG. 4B illustrates a partial side view of the embodiment of the modified RF cannula illustrated in FIG. 4A;

FIG. 9A illustrates a first portion of a flow chart of the method of pain reduction using pulsed RF signals according to the present invention;

FIG. 9B illustrates a second portion of a flow chart of the method of pain reduction using pulsed RF signals according to the present invention;

DETAILED DESCRIPTION OF THE INVENTION

Figure 1:
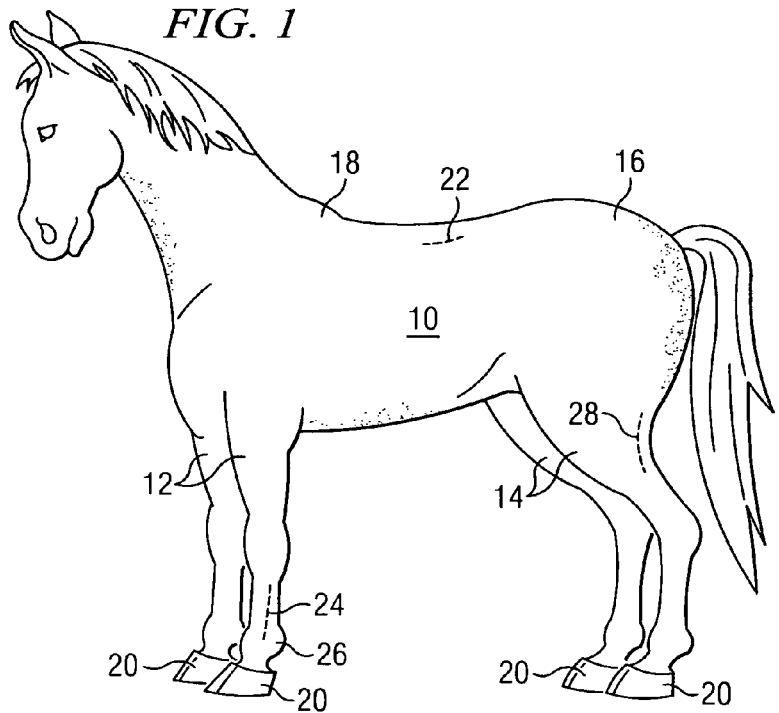
FIG. 1 illustrates a horse showing locations amenable to treatment for pain reduction through the use of pulsed RF electrical signals applied according to the method and apparatus of the present invention.

Referring to FIG. 1, there is illustrated a horse showing some locations amenable to treatment for pain reduction through the use of pulsed RF electrical signals applied according to the method and apparatus of the present invention. The horse 10 is shown having left and right forelegs 12, left and right hind legs 14, a back 16, a withers 18 and hooves 20. Also shown on the horse 10 are the loci for the treatment sites for pain arising in facet joints 22 in paraspinous areas of the back 16, deep flexor tendons 24 and the navicular joint 26 areas in a foreleg 12, and an injury to a high suspensor 28 on the left hind leg 14.

In general the structural features of the nervous system (not shown in FIG. 1) of large mammals is similar to that of humans. For example, it is well known that the central nervous system of mammals includes a sympathetic nervous system and a parasympathetic nervous system. The parasympathetic nervous system includes the autonomic nervous system, which regulates the heart, intestines, glands, etc. The sympathetic nervous system includes the peripheral nerves, which typically lie near the surface of the body of the animal and are involved in sensory reception functions such as touch, heat and cold, and pain.

One class of nerve fibers is known as the ADC peripheral nerve fibers, which are responsible for conducting messages of chronic pain. Other peripheral nerve fibers exist for neuromuscular function, acute pain, proprioception (sensory reception of stimuli in muscles, tendons and joints), etc. The present invention concerns the utilization of pulsed RF energy for the treatment of chronic pain in animals through the neuromodulation of the peripheral nerves that are accessible to the application of RF energy through probes placed percutaneously, i.e., through the skin of the animal's body. The term neuromodulation refers to the deactivation of the ADC peripheral nerve fibers that carry the pain messages to the brain. Although the mechanisms involved in the deactivation of the ADC peripheral nerve fibers through neuromodulation are at present not well understood, it is believed that the presence of the carefully controlled, pulsed RF energy produces neuorchemical changes at the molecular level in the nerve fiber tissues, which inhibit the transmission of impulses along the nerve fiber and result in a reduction in the sensation of pain.

Typical injuries that may be treated using this technique include injuries to various musculoskeletal structures, which meet the following criteria: (1) the injury is long term in nature, i.e., chronic, that has persisted for six months or longer; (2) the injury involves structures that are not critical to sustain mechanical soundness of the animal; (3) the injury has been refractory—not responsive—to traditional therapies; and (4) the injury is located in regions where specific peripheral nerves innervate the region. Some examples of specific conditions might include navicular disease, a gradual deterioration of the navicular bone within the hoof; or an injury to the deep flexor tendon where it attaches to the third phalanx. Other examples may include certain cases of degenerative joint disease where the affected joint is innervated by specific and accessible peripheral nerves.

Another anatomical area of equine patients where neuromodulation using pulsed RF energy may be beneficial is arrears of the back. As with human patients, back problems such as facet joint degeneration, degenerative disc disease and other problems have been successfully treated using this technique. If the specific peripheral nerve can be identified and the RF probe accurately positioned upon the peripheral nerve associated with the pain caused by the underlying injury or disease, these and similar back problems in horses may be successfully treated.

In comparison to some traditional treatments, such as a carbocaine block (injection of a local anesthetic), neuromodulation achieved through pulsed RF signals differs in at least two ways: (1) whereas carbocaine causes complete inactivation of the nerve fiber, pulsed RF lesioning (the technical term for the type of RF signal that is used, to be described in detail hereinbelow) enables the selective deactivation of specific fibers within the nerve; and (2) whereas carbocaine is effective for approximately one hour, pulsed RF lesioning, in treatments performed to date, appears to be effective for months and, in some cases, years. Other benefits include (3) the elimination of side effects from pharmacological intervention and much-improved capacity for rehabilitation due to the absence of pain. Another benefit, particularly for animals participating in regulated or sanctioned competitive events, include elimination of the risk of disqualifications caused by a negative result in a drug test.

In adapting the pulsed RF neuromodulation techniques developed for human patients, several problems had to be overcome before these techniques would be suitable for use with equine patients or other large animals. This experience has also indicates that further development may enable extending the pulsed RF treatment regimes to animals of smaller sizes and possibly for the treatment of a broader range of painful conditions in all animals.

One problem in the prior art that had to be overcome is the presence of hair covering the skin of the animal. This hair requires removal to enable a satisfactory electrical connection to the animal's peripheral nerve system, which includes a ground return path for the signal introduced to the target ADC peripheral nerve fiber. In the conventional prior art method, the skin must be shaved over a large area to permit the attachment of a so-called "grounding pad," a conductive, gel-filled pad connected to a return conductor that provides a low-impedance ground connection through a large surface area. A typical grounding pad for use with bare skin, as used for humans, is approximately eight centimeters wide and fifteen centimeters long and having an effective surface area of approximately 120 square centimeters, or approximately 18.6 square inches. According to the present invention, one solution is the use of two needles, positioned percutaneously through the skin, one or two centimeters apart. The return conductor is then attached to both needles using suitable connectors. Another solution according to the present invention is the use of a specially designed RF cannula that has a broader, oval-shaped tip to provide a greater contact area and a lower Ohmic value when inserted percutaneously through the skin of the animal being treated. Both solutions will be described in detail in the following description.

Another problem in the prior art to be overcome is to determine the values of the various RF signal parameters that are most suited to animal patients. Parameters such as carrier frequency, pulse repetition rate, pulse duration, pulse amplitude, the amounts of energy, the duration of the signal application, the temperature of the affected tissues and the impedance values of the RF probe contacts all had to be evaluated and adapted to the anatomical characteristics of the equine patient. In the prior art, these signals are provided by RF signal generators such as the model RFG-3C Plus Lesion Generator, manufactured by Radionics, a division of Tyco Healthcare Group LP, Burlington, Mass. 01903. This device is designed for pulsed RF neuromodulation treatment of human patients. While positive results on equine patients have been demonstrated using the RFG-3C and the device is presently being used for equine treatments, some of its parameters must be modified and the range of signal energies expanded to optimize its use with horses. Further improvements in the areas of programmability and automated control, for example, will provide instruments better suited to large animal therapies.

Another problem in the prior art is the technique itself. Although all mammalian peripheral nerves are similar in physiology and anatomy, there are significant differences as to size, sensitivity and structure among various species, which limit the adaptability of human treatment techniques to horses. For example, as explained previously, the design of the RF cannula and the grounding techniques had to be modified for use with equine patients. The technique of using such modified probe instruments is also subject to development because of the specific anatomical variations noted hereinabove. Further, though not well understood, variations in microanatomy or neurochemistry appear to give rise to variations in the techniques used.

Figure 2:
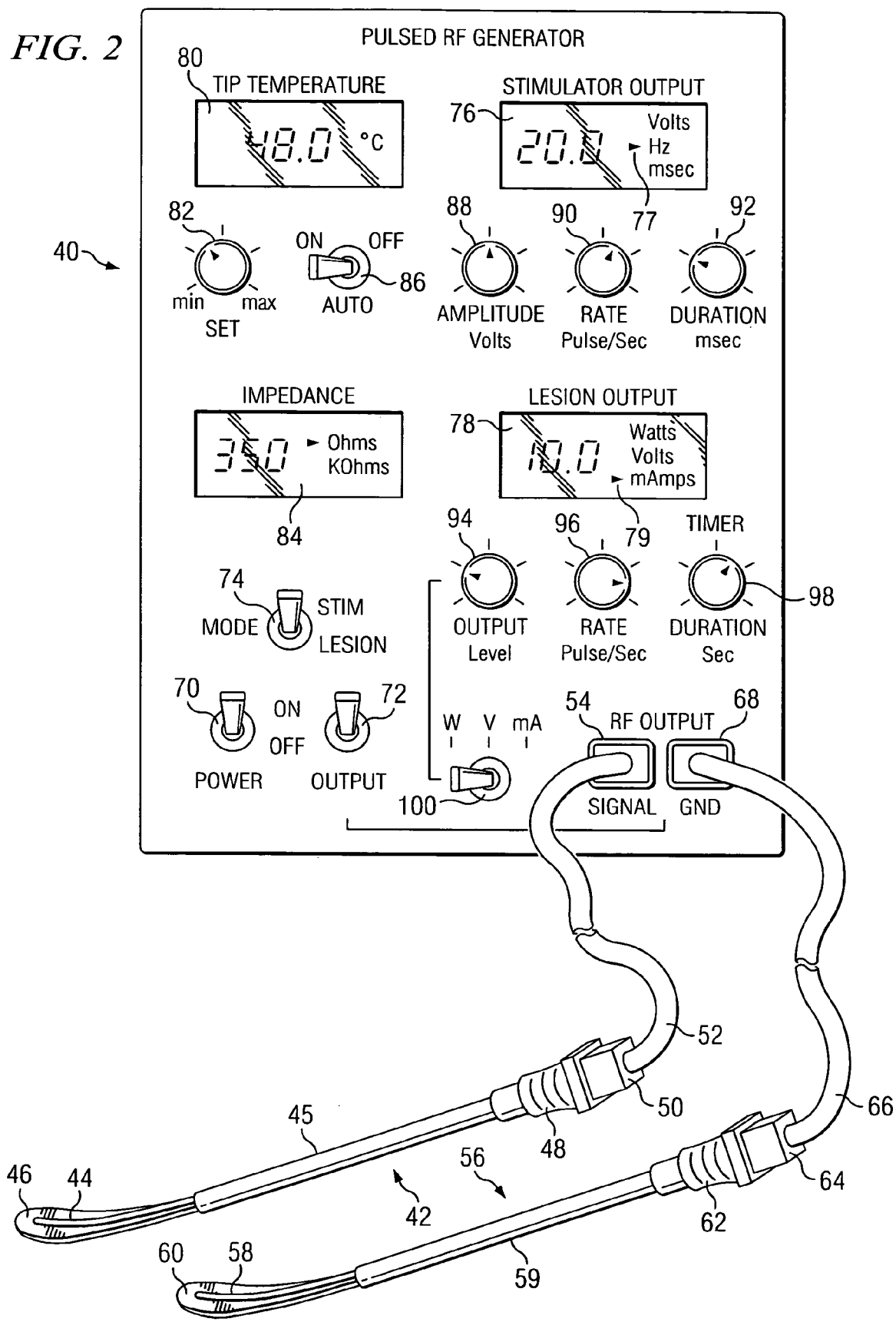
FIG. 2 illustrates one embodiment of a pulsed RF generator equipped with active and dispersive probes according to the present invention.

Referring to FIG. 2, there is illustrated one embodiment of a pulsed RF generator 40 equipped with active 42 and dispersive 56 probes according to the present invention. The active probe 42, also referred to as an active RF cannula 42, includes a tubular tip 44 covered with insulation 45 (typically teflon) along most of its length and a spatulate blade 46 attached to a dorsal side of a portion of the tubular tip 44 not covered by the insulation 45. Attached to the opposite end of the RF cannula 42 is a cannula hub 48, which is configured to receive a connector 50 that terminates an RF signal conductor 52. The signal conductor 52 is a connecting link to an RF signal output terminal 54 of the pulsed RF generator 40. The dispersive probe 56, also referred to as a dispersive RF cannula 56, includes a tubular tip 58 covered with insulation 59 (typically teflon) along most of its length and a spatulate blade 60 attached to a dorsal side of a portion of the tubular tip 58 not covered by the insulation 59. Attached to the opposite end of the dispersive RF cannula 56 is a cannula hub 62, which is configured to receive a connector 64 that terminates an RF ground conductor 66. The ground conductor 66 is a connecting link to an RF ground output terminal 68 of the pulsed RF generator 40.

Continuing further with FIG. 2, the pulsed RF generator 40 includes a power switch 70 and an output switch 72, each providing ON/OFF control, and a mode switch 74. The mode switch enables selection of a stimulator mode or a lesioning mode of operation of the pulsed RF generator 40. A stimulator output display 76 provides readouts calibrated in units of volts, Hertz or milliseconds to indicate values of stimulator mode output signals (or parameters). Similarly, a lesion output display 78 provides readouts calibrated in units of watts, volts and milliamperes to indicate values of lesioning mode output signals (or parameters). A temperature display 80 provides readouts calibrated in degrees Centigrade to indicate values of the tip temperature, i.e., the temperature of the tubular tip 44 of the active RF cannula 42 in contact with the tissues of the animal into which the active RF cannula 42 is placed. The readout shown in the illustrated embodiment is 48.0 degrees Centigrade. A set control 82 enables a user to set the maximum value of the tip temperature that will be reached by the heating effect of the pulsed RF energy output from the pulsed RF generator 40. An impedance display 84 provides readouts calibrated in Ohms or KiloOhms (Kohms) to indicate values of the impedance of the electrical connection with the body of the animal measured between the tubular tips 44, 58 of the respective active 42 and dispersive 56 RF cannulas. The readout shown in the illustrated embodiment is shown as 350 Ohms. An auto control switch enables on/off control of a feature of the pulsed RF generator 40 that regulates the RF signal output level provided at the RF output terminals 54, 68 so that the set value of the tip temperture is not exceeded.

Continuing further with FIG. 2, the stimulator mode output (parameter) values are set and adjusted using the controls placed just below and indicated by the stimulator output display 76. In the illustrated embodiment, the stimulator output display 76 indicates a pulse repetition rate of 20.0 Hertz (Hz) or 20.0 pulses per second. Amplitude control 88 varies the amplitude in volts of the RF output pulses that are provided at the RF signal output terminal 54 relative to the RF ground terminal 68 of the pulsed RF generator 40. Rate control 90 varies the pulse repetition rate in pulses per second of the output signal. Duration control 92 varies the length of time that the pulse train of RF signal pulses is applied through the active 42 and dispersive 56 RF cannulas to the tissues of the animal. In this embodiment, each individual control 88, 90 and 92 may include a momentary push switch to change the units shown on the stimulator display 76. Thus, for example, momentarily pressing the amplitude control 88 changes the display to show the readout in volts. Similarly, momentarily pressing the rate 90 and duration 92 controls changes the displayed units to, respectively, pulses per second (pulse/sec) or milliseconds. The controls for the stimulator output, the amplitude control 88, rate control 90 and the duration control 92 may include an arrowhead indicator 77 on the display 76, which moves to the unit legend of the display to indicate the selected control and units.

Continuing with FIG. 2, the lesion mode output (parameter) values are set and adjusted using the controls placed just below and indicated by the lesion output display 76. In the illustrated embodiment, the lesion output display indicates an output current parameter value of 10.0 milliamperes. Output control 94 varies the power level in watts of the RF output pulses that are provided at the RF signal output terminal 54 relative to the RF ground terminal 68 of the pulsed RF generator 40. Rate control 96 varies the pulse repetition rate in pulses per second of the output signal. Duration control 98 sets a timer, which varies the length of time in seconds that the pulse train of RF signal pulses is applied through the active 42 and dispersive 56 RF cannulas to the tissues of the animal. In some applications this control may enable values measured in units of minutes or other units may be included. The output control 94 in the illustrated embodiment is coupled with an output level range switch 100, which changes the units of measurement shown on the lesion output display 78. Thus, the output level of the lesion output may be indicated in units of watts (W) of power, volts (V) of amplitude, or milliamperes (mA) of current. The lesion mode of the pulsed RF generator 40 is capable of providing stronger signals to the tissues being treated. Therefore, the illustrated embodiment provides the ability to exert precise control over the parameter values being used. It is important to note that the energy levels applied to the patient during pulsed RF neuromodulation are to be kept below those levels that would result in ablation, and hence, permanent damage to the tissues. As in the controls for the stimulator output, the output control 94, rate control 96 and the duration control 98 may include momentary push switches to change the units of the lesion output display 78. Similarly, an arrowhead indicator 79 moves to the unit legend of the display 78 to indicate the selected control and units.

Referring to FIG. 3, which is not drawn to scale, there is illustrated a prior art RF cannula 110 having a tubular tip 112 that is insulated with a teflon coating 114 along most of its length. The tubular tip 112 is fabricated of a material which is an electrical conductor. A typical cannula of the type illustrated in FIG. 3 is approximately 13 centimeters (13 cm) long overall. The tubular tip 112, which extends approximately 1.0 centimeter (1.0 cm) from the teflon insulated portion 114 and has a diameter of approximately 0.8 millimeter (0.8 mm), includes an orifice 116 for introducing a fluid substance into the tissues into which the cannula 110 is inserted. The fluid substance, such as an anesthetic, is forced through the tubular tip 112 and the orifice 116 at predetermined times during a procedure using the cannula 110 as will be described hereinbelow. The tubular tip 112 further includes a blunt end 118, which is typically formed to close the end of the tubular tip 112 in a smooth manner. The exposed portion of the tubular tip 112 of the illustrated embodiment is slightly curved about a radius of approximately 2.5 cm through an arc of approximately 20 to 30 degrees to facilitate insertion and placement into the tissues of the human patient being treated. The opposite end of the prior art RF cannula 110 includes a cannula hub 120 having a cylindrical receptacle portion 122 for receiving a thin wire electrode or, typically, the tip of a syringe, neither of which is shown in FIG. 3 but will be described hereinbelow. The hub 120 includes a lip extension 124 that encircles the receptacle end 122 of the hub 120 and is used to threadingly mate with a device having a Luer tip receptacle (not shown). The illustrated prior art RF cannula is similar to a type C-1010BR, 20 gauge "curved blunt radio frequency cannula" having a 10 cm length and a 10 mm active tip, which is distributed by Precision Medical Engineering, Middleton, Mass. 01949.

Referring to FIG. 4A, which is not drawn to scale, there is illustrated a plan view of one embodiment of an RF cannula modified according to the present invention. The RF cannula 130 includes a tubular tip 132 that is insulated with a teflon coating 134 along most of its length. The tubular tip 132 is fabricated of material that is an electrical conductor. An RF cannula of the type illustrated in FIG. 4A is approximately 13 centimeters (13 cm) long overall. The tubular tip 132, which extends approximately 1.0 centimeter (1.0 cm) from the teflon insulated portion 134 and has a diameter of approximately 0.8 millimeter (0.8 mm), includes an orifice 136 for introducing a fluid substance into the tissues of an equine patient into which the RF cannula 130 is inserted. The fluid substance, such as an anesthetic, is forced through the tubular tip 132 and the orifice 136 at predetermined times during a procedure using the RF cannula 130 as will be described hereinbelow. The tubular tip 132 further includes a blunt end 138, which is typically formed to close the end of the tubular tip 132 in a smooth manner. The exposed portion of the tubular tip 132 of the illustrated embodiment is slightly curved about a radius of approximately 2.5 cm through an arc of approximately 20 to 30 degrees to facilitate insertion and placement into the tissues of the equine patient being treated.

The RF cannula 130 illustrated in FIG. 4A includes a modification to the exposed end of the tubular tip 132. Attached to a dorsal side (see FIG. 4B) of the exposed end of the tubular tip 132 is a spatulate blade 140. The spatulate blade 140 is a flat, blade-shaped extension conformably attached to the dorsal side of the tubular tip 132 so that it also is slightly curved to approximately the same radius as the exposed portion of the tubular tip 132. Notice also that the spatulate blade 140 is on the opposite side of the tubular tip 132 from the orifice 136. Further, the spatulate blade 140 has a width across the widest part of approximately 2.0 mm and the rounded, oval-shaped end 142 extends past the blunt end 138 of the exposed portion of the tubular tip 132 for the illustrated embodiment. The end 142 of the RF cannula 130 is not limited to an oval shape. Generally, any shape may be used; preferably the shape of the end 142 should not include sharp edges or points. The opposite end of the RF cannula 130 includes a cannula hub 144 having a cylindrical receptacle portion 146 for receiving a thin wire electrode or, typically, the tip of a syringe, neither of which is shown in FIG. 4A but will be described hereinbelow. The hub 144 includes a lip extension 148 that encircles the receptacle end 146 of the hub 144 and is used to threadingly mate with a device having a Luer tip receptacle (not shown).

Referring to FIG. 4B, which is not drawn to scale, there is illustrated a partial side view of the embodiment of the modified RF cannula illustrated in FIG. 4A wherein the same reference numbers indicate like structures. FIG. 4B shows the slight curvature of the exposed portion of the tubular tip 132 as described hereinabove and the conformably attached spatulate blade 140, which extends past the blunt end 138 of the exposed portion of the tubular tip 132 by approximately 1.0 mm.

Figure 5:
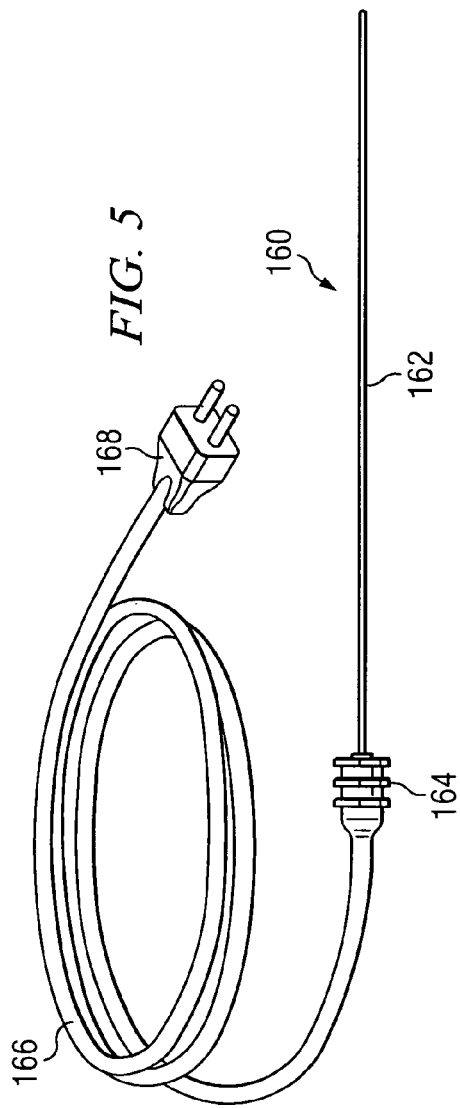
FIG. 5 illustrates a pictorial view of one embodiment of an RF electrode or stylette coupled to a connector via a conductor, for use with the RF cannula of FIG. 4 of the present invention.

Referring to FIG. 5, there is illustrated a pictorial view of one embodiment of an RF electrode or stylette assembly 160 coupled to a connector via an insulated conductor, for use with the RF cannula 130 of FIGS. 4A and 4B of the present invention. The electrode assembly includes a conductive wire electrode 162 secured into a hub 164, which is attached to an insulated conductor 166 connected at its opposite end to a connector 168. The hub 164 encloses an electrical connection between the electrode 162 and a conductive wire (not shown) extending within the insulated conductor 166 to the connector 168, to form an electrical circuit with the connector 168, which is inserted into a mating receptacle for the RF signal 54 or ground 68 output terminal on the pulsed RF generator 40. The electrode 162 has a diameter small enough, e.g., 28 or 30 gauge wire (approximately 0.25 mm to 0.35 mm) to be easily inserted into the hollow interior of the tubular tip 132 of the RF cannula 130 shown in FIGS. 4A and 4B. The wire electrode 162 is a little shorter than the tubular tip 132, so that it reaches just past the orifice 136, i.e., it is visible through the orifice just as the wire electrode is fully inserted within the tubular tip 132. The wire electrode 162 enables an electrical connection to be made between the output 54, 68 of the pulsed RF generator and the tubular tip 132, which makes an electrical connection with the tissue of the patient.

Figure 6:
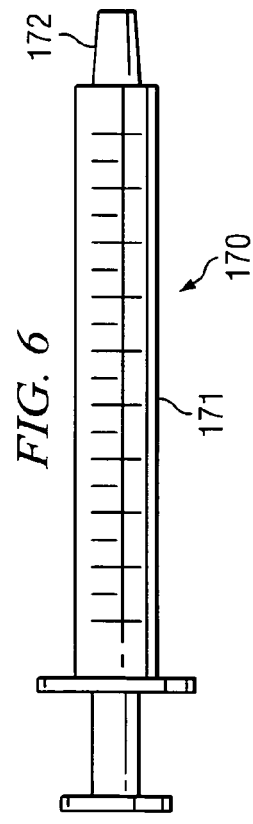
FIG. 6 illustrates one embodiment of a small syringe for use with the RF cannula of FIG. 4 of the present invention.

Referring to FIG. 6, there is illustrated one embodiment of a small syringe for use with the RF cannula 130 of FIG. 4 of the present invention. The small syringe 170 illustrated includes a body 171 having a capacity of approximately 1.0 milliliter (1.0 ml) and an outlet tip 172 sized and configured to fit within the receptacle 146 of the RF cannula of FIG. 4A. The small syringe 170 may be used for injecting a local anesthetic into the RF cannula 130 during a treatment procedure to be described hereinbelow in conjunction with FIG. 9.

Figure 7:
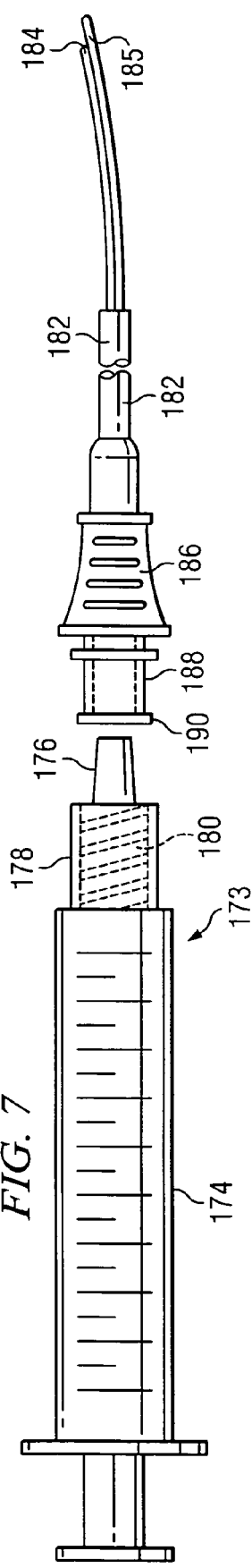
FIG. 7 illustrates one embodiment of a syringe equipped with a Luer tip and one embodiment of the RF cannula of FIG. 4 of the present invention.

Referring to FIG. 7, there is illustrated another embodiment of a syringe, this one being equipped with a Luer tip and shown with one embodiment of the RF cannula 130 of FIG. 4 of the present invention. The syringe 173 includes a body 174 having a capacity of, e.g., six ml, an outlet tip 176 and a Luer tip 178. The Luer tip 178 is a hollow cylindrical receptacle that partially encloses the outlet tip 176 of the syringe 173 and includes a spiral-shaped ramp 180 disposed around an inside wall of the Luer tip 178. The spiral ramp 180 acts as an internal thread, which permits the lip extension of a mating hub formed on an RF cannula to be inserted and rotated in the manner of a machine screw into the Luer tip 178. For example, referring further to FIG. 7, an RF cannula 182 according to the present invention, including a tubular tip 184 having a conformably attached spatulate blade 185 and a hub 186, also has a cylindrical receptacle 188 configured with a lip extension 190 encircling the cylindrical receptacle 188. The RF cannula is slipped over the outlet tip 176 of the syringe 173 and rotated clockwise such that the lip extension engages the spiral-shaped ramp 180, permitting the RF cannula 182 and the syringe 173 to be secured together in a liquid-tight joint when the RF cannula 182 is fully rotated into the Luer tip 178 of the syringe 173. As will be described further hereinbelow, the syringe will be used to inject a carbocaine block anesthetic into the patient tissues during a treatment procedure.

Figure 8:
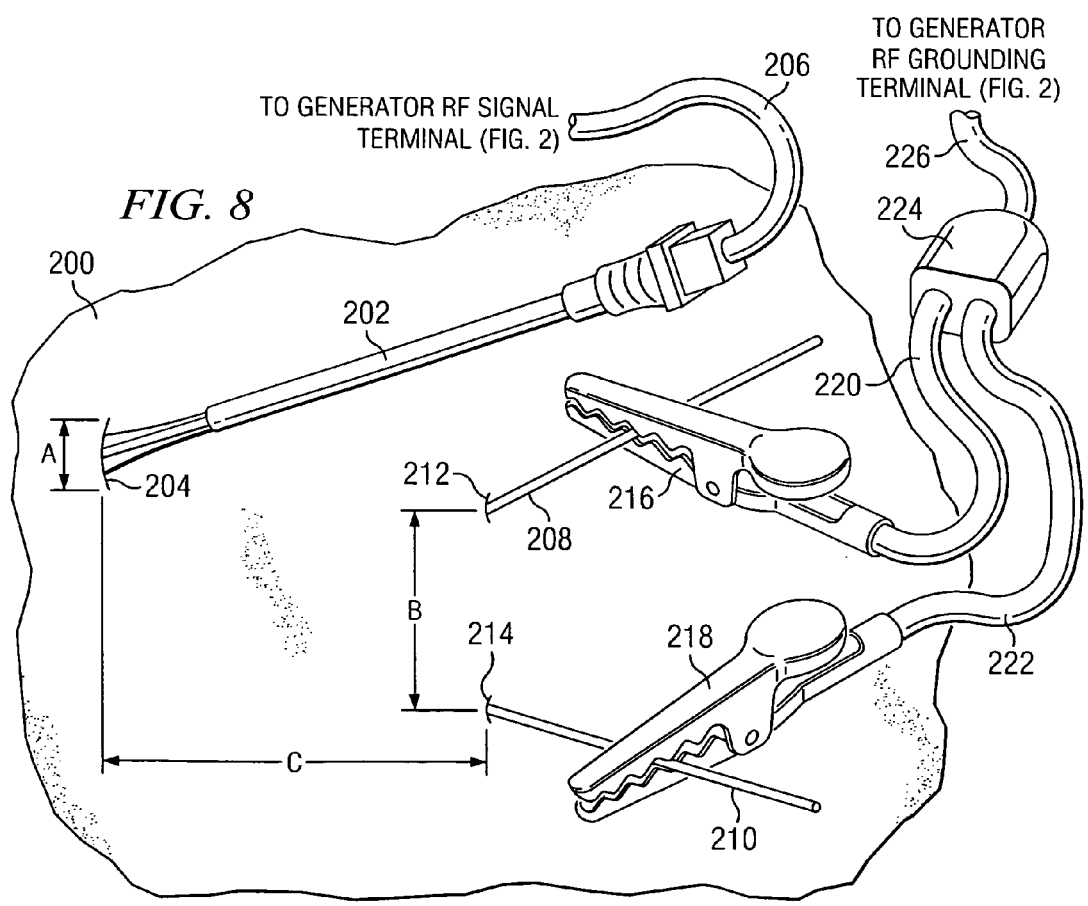
FIG. 8 illustrates a pictorial view of one embodiment of active and dispersive probes in use on a patient according to the present invention.

Referring to FIG. 8, there is illustrated a pictorial view of one embodiment of active and dispersive probes in use on a patient according to the present invention. A segment 200 of an equine patient's skin is shown in FIG. 8 including an RF cannula 202 used as an active probe and a pair of needles 208, 210 used together as a dispersive probe. In lieu of the pair of needles 208, 210, another RF cannula such as the one shown at 202 could be used, located approximately between the locations 212 and 214 on the segment 200 of the patient's skin and connected to the pulsed RF generator's RF ground terminal (see FIG. 2) in the same manner as the RF cannula 202. FIG. 8 thus illustrates an alternative to a grounding connection provided by an RF cannula used as a dispersive probe.

Continuing with FIG. 8, the active probe, RF cannula 202, coupled to the RF signal output 54 of the pulsed RF generator 40 (see FIG. 2) via the conductor 206, is inserted into a small incision 204 (the location of this incision will also be called the active probe site 204 during the description of the procedure illustrated in FIG. 9) in the skin as close as possible to the target ADC peripheral nerve location. The incision, made after suitable antiseptic and anesthetic preparation as will be described, is approximately 0.5 cm long (dimension "A") in a typical case. The spatulate blade of the active probe 202 is positioned so that it is just against the ADC peripheral nerve, being careful to avoid nicking or otherwise injuring the fibers along the surface of the nerve bundle. The dispersive probe, here shown as the pair of needles 208, 210, are positioned approximately one or two cm apart (dimension "B"), a distance of approximately 8 to 10 cm (dimension "C") from the incision site for the active probe. The purpose of the dispersive probe is to provide a suitable ground return connection for the RF signal output from the pulsed RF generator 40. Two needles are used, inserted percutaneously after suitable antiseptic and anesthetic preparation, and connected in parallel to ensure that a low impedance connection is provided. In most cases, it has been found that the impedance, as indicated by the impedance readout of the pulsed RF generator 40, should be kept below 350 Ohms for the best results. The needles 208, 210 are coupled to the conductor 226 via respective alligator clips 216, 218 and leads 220, 222, and a coupling hub 224. The conductor 226 is coupled to the RF ground terminal 68 on the pulsed RF generator 40. If an RF cannula is to be used as the dispersive probe, it is placed through an incision in the skin in the same manner as the RF cannula 202 is placed in the incision 204.

Referring to FIG. 9A, there is illustrated a first portion of a flow chart procedure 250 of the method of pain reduction using pulsed RF signals according to the present invention. The method begins at a start block 252 wherein the diagnosis has been made and all necessary equipment and personnel are assembled and positioned for convenient use and operation in the treatment space. In step 254, a suitable RF lesion generator such as the pulsed RF generator 40 is prepared by running through a suitable checklist of test routines to verify proper operation. At this point, the parameter values of the pulsed RF signals may be preset to their initial settings, making sure that the output switch 72 is turned off and the amplitude control 88 and the output level control 94 are set to their minimum settings before adjusting any of the other controls. It is important that no signals be applied to the patient until the active and dispersive probes are properly positioned and the electrical impedance verified in the following steps. After the pulsed RF generator 40 is prepared in step 256, the site of the ADC peripheral nerve associated with the painful condition is located on the patient's skin. In many cases this step can be accomplished by palpation of the surface tissues and observation of the reactions of the horse to locate the peripheral nerve of interest. In other cases it may be necessary to employ a fluoroscope to view real time X-ray images after injecting a small amount of contrast media into the tissues to identify the nerve path.

Continuing with the procedure 250 of FIG. 9A, aseptic preparation of the active and dispersive probe sites is performed in step 258. Next, in step 260, the probe sites are desensitized using a carbocaine nerve block applied to the site locations. In step 262, incisions are made at the site locations and RF cannulas are inserted into the incisions at the active and dispersive sites. The active RF cannula 42 must be inserted with special care to properly locate the spatulate blade 46 of the active RF cannula 42 without damaging the peripheral nerve. The spatulate blade 46 is positioned with its tip alongside and in contact with the surface of the peripheral nerve. The dispersive RF cannula 56 is also inserted carefully into the incision so that the spatulate blade 60 is fully in contact with the tissues just beneath the skin in order to make a reliable ground return connection with the pulsed RF generator 40. In an alternative procedure to step 262, instead of using an RF cannula as the dispersive probe, two needles 208, 210 (see FIG. 8, described previously) are inserted percutaneously through the skin at locations 212, 214. The electrical connection is then made to the needles 208, 210 using the alligator clips 216, 218 as illustrated in FIG. 8 or other suitable connectors attached to the dispersive conductor 226.

Continuing with FIG. 9A, after the active and dispersive RF cannulas are properly placed on the patient in step 262, the active and dispersive RF electrodes are inserted into their respective RF cannulas in step 264 to enable the measurement of the electrical impedance of the connection to the patient. As described previously, the impedance is displayed on the Impedance readout 84 of the pulsed RF generator 40. The reading is satisfactory if it is below approximately 350 Ohms. A higher value indicates excessive impedance, requiring that one or both of the active 42 and dispersive 56 probes must be repositioned before the procedure 250 may be resumed. During the application of the pulsed RF signals in the subsequent steps to be described, the electrical impedance should be monitored to ensure that the indicated parameter values for the amplitude or output levels of the pulsed RF signals are accurate. Failure to perform the procedure with the electrical impedance below 350 Ohms could result in injury to the patient or a failed result of the treatment.

In step 266 the pulsed RF generator 40 is set to the Stimulator mode using the mode switch 74. This mode is used to determine the sensory threshold of the patient and to locate the correct ADC peripheral nerve fibers involved in the patient's sensation of pain caused by the underlying injury or disease. With the amplitude control 88 set to its minimum setting, the parameter values are set. For treatment of pain associated with a leg or back injury or disease, the settings are as follows: pulse repetition rate=10 Hz., pulse duration=10 msec. and the tip temperature limit is set to 48 degrees Centigrade (deg. C.) when treating horses. However, the tip temperature setting may be varied between 43 deg. C. and 55 deg. C. In step 268, the amplitude is gradually increased while observing the responses of the patient to determine the threshold of sensation and whether the affected peripheral nerve has been correctly selected. In a typical equine patient, the amplitude may be in the range of 3 to 6 volts as the threshold of sensation is approached. At decision step 270, a determination is made whether the probe sites are correctly verified before proceeding with the procedure 250. If the determination is negative, the next step performed is step 272, to remove the pulsed RF generator 40 output, and to perform step 274 to recheck the adjustment of the active RF cannula 202 at the active probe site 204 as shown in FIG. 8 and repeat the steps 266, 268 and 270. If the result of step 279 is again negative, the procedure should be aborted to determine the cause and restarted with step 254. During step 270, if the result is affirmative, the procedure flows to step 276 shown in FIG. 9B.

Referring to FIG. 9B there is illustrated a second portion of a flow chart of the method of pain reduction using pulsed RF signals according to the present invention. In step 276, the output amplitude of the pulsed RF generator 40 is reduced using the amplitude control 88 and the active RF electrode (see, e.g., FIG. 5, showing the electrode 160) removed from the active RF cannula 202. Next, in step 278, a small syringe (see, e.g., FIG. 6) loaded with a carbocaine block solution is attached to the RF cannula 202 and a prescribed amount of the solution is injected into the vicinity of the target ADC peripheral nerve fibers to temporarily (e.g., for approximately one hour) block the sensation of pain associated with the underlying injury or disease. Then, in step 280, the syringe is removed, the active RF electrode is reinserted and the electrical impedance is re-verified.

In step 282, the pulsed RF generator 40 is set to the Lesioning (stimulation) mode using the mode switch 74. This mode is used to apply regulated levels of RF pulse energy to the affected ADC peripheral nerve fibers involved in the patient's sensation of pain caused by the underlying injury or disease. With the output level control 94 set to its minimum setting, the parameter values are set. For treatment of pain associated with a leg injury or disease, the typical settings may be as follows: pulse repetition rate=2.0 Hz., pulse duration=20 msec., the timer is set to 5 minutes and the tip temperature limit is set to 48 degrees Centigrade when treating horses. In some cases the timer may be set to 120 seconds, repeated at three minute intervals for three cycles instead of continuously for five minutes.

For treatment of pain associated with a back injury or disease, the settings made in step 282 may be as follows: pulse repetition rate=500 Hz., pulse duration=1.0 msec., the timer for continuous output of 70 seconds and a tip temperature of 80 degrees Centigrade. The Auto switch is set to the ON position The output level is gradually increased until the tip temperature reaches 80 degrees Centigrade and thereafter regulated to maintain that tip temperature until the timer interrupts the RF output while the patient responses are being monitored during the preset interval in step 284. In some applications, such as may occur where considerable experience demonstrates the efficacy thereof, the output level may be controlled manually using the output level control 94, which enables user-adjustment of the output level within the range of zero to ten volts (amplitude of the pulse signal), or zero to 50 watts of RF power, or zero to 100 milliamps of current.

In some cases the protocol of the preset procedure is repeated one or more times. The determination to do so is made in decision step 286. If the procedure is not to be repeated, the flow advances to step 288, wherein the pulsed RF generator output is reduced to zero (if it was manually increased during the procedure), the RF electrodes removed, the RF cannulas removed and the skin cleaned and the small incision wounds treated. Thereafter, the procedure 250 ends at step 290. Returning to decision step 286, if the result of the determination is that the preset procedure is to be repeated, the flow advances to step 292 to await a predetermined amount of time, according to the protocol for the particular treatment, before the procedure 250 is repeated. In such a case, after the prescribed time has elapsed, the flow returns to the start block 252 in step 294. In some cases only a part of the procedure 250 may need to be repeated; in those cases the flow advances from step 294 to an insertion point. The insertion point may occur at steps 264 or 276, for example.

Figure 10:
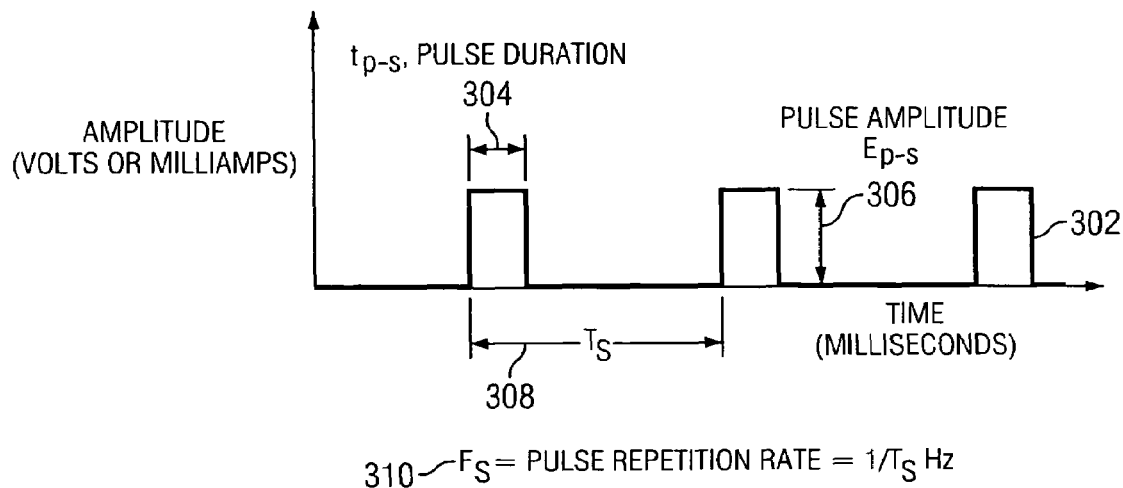
FIG. 10 illustrates one embodiment of a pulse waveform for use in the method of pain reduction according to the present invention.

Referring to FIG. 10, there is illustrated one embodiment of a pulse waveform for use in the method of pain reduction according to the present invention. A graph is shown, having a vertical axis labeled in amplitude units such as volts or milliamperes and a horizontal axis labeled in time units such as milliseconds. A generalized pulse waveform 302 is defined by parameters such as pulse duration 304, represented by the symbol tp, the amount of time the pulse is held at a non-zero value. The amplitude of the pulse 302 is represented by the symbol Ep-s and the period of one cycle of the pulse 308 is represented by the symbol Ts. The frequency, or repetition rate 310, represented by the symbol Fs, is the reciprocal of the period 308, or 1/Ts. The subscript "s" in the foregoing sysmbols means that the symbols define parameters of the Stimulator pulse waveforms. In a typical pulse RF generator 40, such as the RFG-3C mentioned previously, the values for Fs are from a one-shot pulse to 200 Hz; for tp are from 0.1 msec to 1.0 msec; and for amplitude Ep-s, selectable from zero to 10 volts or, zero to 10 milliamperes in a constant current mode.

Figure 11:
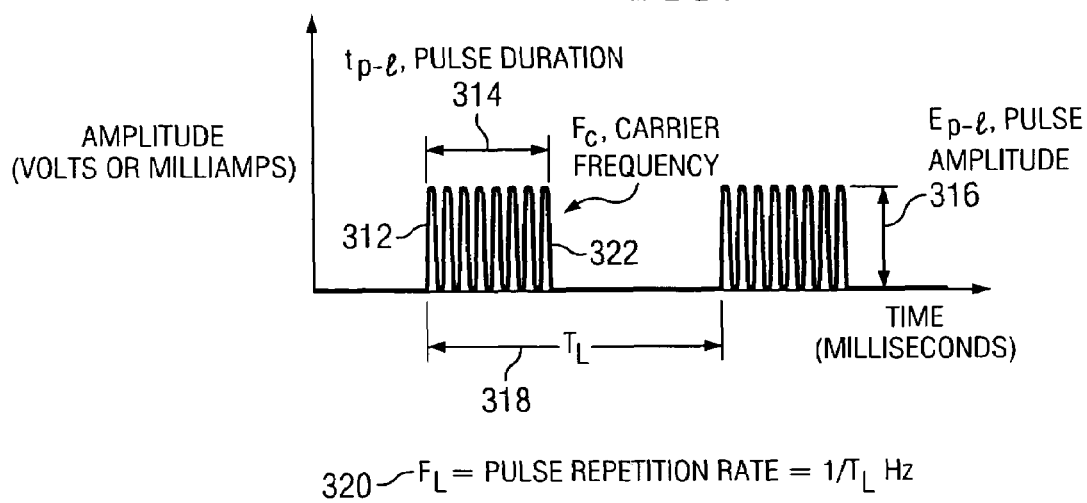
FIG. 11 illustrates another embodiment of a pulse waveform for use in the method of pain reduction according to the present invention.

Referring to FIG. 11, there is illustrated another embodiment of a pulse waveform for use in the method of pain reduction according to the present invention. The waveform illustrated in FIG. 11 represents a signal provided by the pulsed RF generator 40 when operating in the RF Lesioning mode, as set by the mode switch 74. A graph is shown, having a vertical axis labeled in amplitude units such as volts or milliamperes and a horizontal axis labeled in time units such as milliseconds. A generalized pulse waveform 312 is defined by parameters such as pulse duration 314, represented by the symbol tp-l, the amount of time the pulse is held at a non-zero value. The amplitude of the pulse 312 is represented by the symbol Ep-l and the period of one cycle of the pulse 318 is represented by the symbol Tl. The pulse frequency, or repetition rate 320, represented by the symbol Fl, is the reciprocal of the period 318, or 1/Tl. The pulsed RF signals output in the Lesioning mode include a carrier frequency, Fc. Thus, the output pulse waveform consists of a modulated, high frequency carrier signal. In the case of the RFG-3c, the carrier frequency, Fc, is 500 kiloHertz (500 KHz.). The subscript "l" (the letter 'l') in the foregoing sysmbols means that the symbols define parameters of the Lesioning pulse waveforms. In a typical pulse RF generator 40 operating in the pulsed lesioning mode, such as the RFG-3C mentioned previously, the values for Fl are from 1.0 to 8.0 Hz; for tp-l are from 10 msec to 30 msec; and for amplitude Ep-l, selectable from zero to 100 volts or, zero to 999 milliamperes. The maximum output power in Lesioning mode is 50 watts. The timer may be set for values from zero to 20 minutes.

A method and apparatus for reducing chronic pain in animals by radio frequency (RF) neuromodulation of peripheral nerves of the animal has been disclosed. The method, using the disclosed apparatus, comprises the steps of attaching active and dispersive percutaneous probes at respective active and dispersive locations relative to a peripheral nerve of the patient associated with the pain to be reduced; generating a first pulsed RF signal for coupling to the active and dispersive probes to verify the location of the peripheral nerve; and generating a second pulsed RF signal for coupling to the active and dispersive probes to modify propagation of pain sensation in the peripheral nerve without ablation thereof. In one embodiment of the apparatus, the active percutaneous probe includes an RF cannula having a conductive spatulate blade conformably attached to a dorsal side of a curved, blunt-ended tubular tip portion of the RF cannula. In another embodiment of the apparatus, a dispersive percutaneous probe includes a pair of 22 gauge needles connected to ground return conductors. In yet another embodiment of the apparatus, a pulsed RF generator is modified to provide specific outputs adapted to the neuromodulation of peripheral nerves in veterinary patients.

The foregoing description, when read in conjunction with the attached drawings, describes several preferred embodiments of the present invention to illustrate the principles of the invention. Variations in structure and function of the embodiments illustrated are contemplated that will be apparent to those skilled in the art yet still fall within the scope of the invention set forth in the appended claims.

What is claimed is:

1. A method of reducing chronic pain in animals by radio frequency (RF) neuromodulation of peripheral nerves of the animal, comprising the steps of:
    placing an active and a dispersive percutaneous probe at respective active and dispersive locations against a peripheral nerve of the animal associated with the pain to be reduced;
    generating a first pulsed RF signal configured according to a first protocol for coupling to the active and dispersive probes via conductive leads to verify the location of the peripheral nerve; and
    generating a second pulsed RF signal configured according to a second protocol for coupling to the active and dispersive probes via the conductive leads after the first pulsed RF signal is withdrawn, to modify propagation of pain sensation in the peripheral nerve without ablation thereof; wherein
    at least the active percutaneous probe includes an RF cannula having an elongated conductive spatulate blade conformably attached to a dorsal side of a curved, blunt-ended tubular tip portion of the RF cannula.

2. The method of claim 1, wherein the step of placing comprises the step of:
    placing the active and dispersive percutaneous probes at respective locations of a peripheral nerve associated with pain occurring in the legs or back of animals.

3. The method of claim 1, wherein the step of placing comprises the step of:
    placing the active and dispersive percutaneous probes at respective locations of a peripheral nerve associated with pain occurring in the legs or back of animals of the family equinidae.

4. The method of claim 1, wherein the step of placing comprises the step of:
    placing the active and dispersive percutaneous probes at respective locations of a peripheral nerve associated with pain occurring in the legs or back of animals of the family equinidae, including chronic pain associated with at least one selected from the group consisting of deep digital flexor tendon, navicular disease, degenerative joint disease and high suspensor structures in the legs and facet joint degeneration and degenerative disc disease in spinal structures of the back.

5. The method of claim 1, when being employed to treat pain in a large animal patient, wherein the step of generating a first pulsed RF signal is replaced by the step of palpating surface tissues of the large animal patient to verify location of the peripheral nerve associated with the pain to be reduced.

6. The method of claim 1, wherein the step of attaching further comprises the steps of:
    preparing the active and dispersive locations for placing the active and dispersive probes to the patient; and
    placing the active and dispersive probes in the respective active and dispersive locations of the patient.

7. The method of claim 6, wherein the step of preparing comprises the steps of:
    determining the active location of the skin of the patient proximate a peripheral nerve of the patient associated with the pain to be reduced;
    determining the dispersive location on the skin of the patient within approximately ten centimeters of the active location;
    preparing the active and dispersive locations antiseptically;

applying a topical anesthetic to the active and dispersive locations of the skin; and making an incision in the patient's skin in at least the active and dispersive locations.

8. The method of claim 6, wherein the step of placing comprises the steps of:

inserting a first RF cannula having the spatulate blade into the skin of the patient at the active location;

inserting a second RF cannula at the dispersive location; and inserting RF electrodes into the first and second RF cannulas at the respective active and dispersive locations to establish an electrical connection between the active and dispersive locations; and measuring the electrical impedance between the active and dispersive locations to verify that the impedance is below a predetermined limit.

9. The method of claim 8, wherein the step of placing further comprises the step of:

checking the insertion of the first and second RF cannula; and repeating the measurement of the electrical impedance.

10. The method of claim 6, wherein the step of placing further comprises the steps of:

inserting a first RF cannula having the spatulate blade into the skin of the patient at the active location;

inserting first and second needles at the dispersive location; and inserting an RF electrode into the first RF cannula at the respective active location and connecting dispersive signal leads to the first and second needles at the dispersive location to establish an electrical connection, including tissues of the patient, between the active and dispersive locations; and measuring the electrical impedance between the active and dispersive locations to verify that the impedance is below a predetermined limit.

11. The method of claim 10, wherein the step of placing further comprises the step of:

checking the insertion of the first and second RF cannula; and repeating the measurement of the electrical impedance.

12. The method of claim 1, wherein the step of generating a first pulsed RF signal comprises the steps of:

configuring an RF signal generator having an output for operation in a stimulator mode;

setting signal parameters according to the first protocol;

connecting active and dispersive signal leads from output terminals of the RF signal generator to the respective active and dispersive probes; and gradually applying the first pulsed RF signal output while monitoring a response of the patient to verify correct location of the active and dispersive probes.

13. The method of claim 12, wherein the stimulator mode comprises a first protocol limited to stimulating the peripheral nerve of the patient within a sensory range for the patient below a normal threshold of pain.

14. The method of claim 12, wherein the step of generating a first pulsed RF signal further comprises the step of:

removing the output of the RF signal generator if monitoring the response of the patient during the step of gradually applying the output indicates an incorrect location or signal parameter value.

15. The method of claim 12, wherein the first protocol comprises RF signal parameters including pulse amplitude, pulse repetition rate and pulse duration, wherein each parameter is characterized by a value.

16. The method of claim 15, wherein typical values for an equine patient include a pulse amplitude adjusted from zero to a threshold of sensation, a pulse repetition rate of approximately 50 Hertz and a pulse duration of approximately 10 milliseconds.

17. The method of claim 15, wherein respective values for pulse amplitude may vary from zero to ten volts, for pulse repetition rate may vary from 1.0 to 500 Hertz and for pulse duration may vary from one-tenth millisecond to 100 milliseconds.

18. The method of claim 15, wherein the pulse repetition rate may be set to provide a one-shot pulse.

19. The method of claim 1, wherein the step of generating a second pulsed RF signal comprises the steps of:

removing an active RF electrode from the active RF cannula after reducing the second pulsed RF signal from an RF generator output to zero;

injecting a predetermined amount of a local anesthetic solution into tissue of the patient proximate the first location using an anesthetic metering device attached to the active RF cannula; and replacing the anesthetic metering device with the active RF electrode and verifying the electrical impedance is below a predetermined limit.

20. The method of claim 19, wherein the local anesthetic solution is a carbocaine nerve block.

21. The method of claim 19, wherein the step of generating a second pulsed RF signal further comprises the steps of:

configuring the RF signal generator having an output for operation in a lesioning mode;

setting signal parameters including according to the second protocol;

verifying connection of the active and dispersive signal leads from output terminals of the RF signal generator to the respective active and dispersive probes; and applying the output according to the second protocol during a preset period while monitoring one or more responses of the patient.

22. The method of claim 21, wherein the step of generating a second pulsed RF signal further comprises the step of:

removing the active RF electrode from the active RF cannula after reducing the RF generator output to zero;

removing the active and dispersive RF cannulas from the patient; and applying a topical agent to the patient's skin after cleaning the area proximate the first and second locations.

23. The method of claim 21, wherein the lesioning mode comprises a second protocol for applying a predetermined RF signal to the peripheral nerve in contact with the active RF probe to modify transmission of nerve impulses conveying chronic pain information.

24. The method of claim 21, wherein the preset period comprises a value from zero to thirty minutes.

25. The method of claim 21, wherein the predetermined limit of the electrical impedance is 350 Ohms.

26. The method of claim 21, wherein the second protocol comprises:

RF signal parameters including pulse amplitude, pulse repetition rate, pulse duration and tip temperature, wherein each parameter is characterized by a value.

27. The method of claim 26, wherein respective values for pulse amplitude may vary from zero to 100 volts or zero to 50 watts or zero to 1.0 ampere, for pulse repetition rate may vary from 1.0 to 500 Hertz, for pulse duration may vary from one-tenth millisecond to 100 milliseconds and for tip temperature may vary from body temperature to 90 Degrees centigrade.

28. The method of claim 26, wherein typical values for an equine patient being treated for pain associated with a leg injury include an RF signal applied for approximately five minutes and having a pulse repetition rate of approximately two Hertz, a pulse duration of approximately twenty milliseconds and an output amplitude controlled to maintain a tip temperature of approximately 48 degrees centigrade.

29. The method of claim 26, wherein typical values for an equine patient being treated for pain associated with a back injury include an RF signal applied for approximately seventy seconds and having a pulse repetition rate of approximately 500 Hertz, applied for a continuous duration and an output amplitude controlled to maintain a tip temperature of approximately 80 degrees centigrade.

30. Apparatus for reducing chronic pain in animals by radio frequency (RF) neuromodulation of a peripheral nerve of the animal, comprising:
   a generator, for generating pulsed RF signals in at least a first mode and a second mode, to be coupled via respective active and dispersive conductors through respective active and dispersive probes placed in respective active and dispersive locations on an animal patient's body, for reducing chronic pain experienced by the animal without ablation of the peripheral nerve;
   a set of RF percutaneous probes including at least an active probe and a dispersive probe placed in the respective active and dispersive locations in the animal's body, at least the active probe further comprising an RF cannula having an elongated conductive spatulate blade conformably attached along a longitudinal axis to a dorsal side of a curved, blunt-ended tubular tip portion of the RF cannula; and
   anesthetic metering device adapted to connect with the active probe, for administering a liquid substance into the tissue of the animal that is in the active location.

31. The apparatus of claim 30, wherein the dispersive probe comprises:
   first and second needles coupled to a common dispersive conductor for providing a return path to the generator for the pulsed RF signals.

32. The apparatus of claim 30, wherein the anesthetic metering device adapted to connect with the active probe for administering a liquid substance into the tissue of the animal that is in the active location includes a syringe.

33. The apparatus of claim 30, wherein the generator comprises:
   a signal generator having user-operated controls, for setting signal parameter values and active and dispersive signal conductors for coupling an output RF signal from the signal generating means to the active and dispersive locations; and
   control means for controlling the RF signal responsive to a predetermined probe tip temperature value.

34. The apparatus of claim 33, wherein the generator further comprises:
   a readout for providing parameter value information to the user; and
   measuring devices for measuring at least the probe tip temperature and a probe impedance between the active and dispersive probes and outputting measured values from the readout means.

35. The apparatus of claim 30, wherein the first mode of the generator comprises:

a first pulsed signal configured according to a first protocol for stimulating the peripheral nerve of the patient within a sensory range for the patient below a normal threshold of pain to verify correct location of the active and dispersive probes.

36. The apparatus of claim 31, wherein the first protocol comprises:
   a plurality of RF signal parameters including pulse amplitude, pulse repetition rate and pulse duration, wherein each signal parameter is characterized by a value.

37. The apparatus of claim 36, wherein typical values for an equine patient include a pulse amplitude adjusted from zero to a threshold of sensation, a pulse repetition rate of approximately 50 Hertz and a pulse duration of approximately 10 milliseconds.

38. The apparatus of claim 36, wherein respective values for pulse amplitude may vary from zero to ten volts, for pulse repetition rate may vary from 1.0 to 500 Hertz and for pulse duration may vary from one-tenth millisecond to 100 milliseconds.

39. The apparatus of claim 36, wherein the pulse repetition rate may be set to provide a one-shot pulse.

40. The apparatus of claim 30, wherein the second mode of the generator comprises:
   a second pulsed signal configured according to a second protocol for applying a predetermined RF signal to the peripheral nerve in contact with the active probe to modify transmission of nerve impulses conveying chronic pain information;
   wherein the second pulsed signal is applied during a preset period while monitoring one or more responses of the patient.

41. The apparatus of claim 40, wherein the second protocol comprises:
   a plurality of RF signal parameters including pulse amplitude, pulse repetition rate, pulse duration and tip temperature, wherein each signal parameter is characterized by a value.

42. The apparatus of claim 41, wherein respective values for pulse amplitude may vary from zero to 100 volts or zero to 50 watts or zero to 1.0 ampere, for pulse repetition rate may vary from 1.0 to 500 Hertz, for pulse duration may vary from one-tenth millisecond to 100 milliseconds and for probe tip temperature may vary from body temperature to 90 Degrees centigrade.

43. The apparatus of claim 41, wherein typical values for an equine patient being treated for pain associated with a leg injury include an RF signal applied for approximately five minutes and having a pulse repetition rate of approximately two Hertz, a pulse duration of approximately twenty milliseconds and an output amplitude controlled to maintain a probe tip temperature of approximately 48 degrees centigrade.

44. The apparatus of claim 41, wherein typical values for an equine patient being treated for pain associated with a back injury include an RF signal applied for approximately seventy seconds and having a pulse repetition rate of approximately 500 Hertz, applied for a continuous duration and an output amplitude controlled to maintain a tip temperature of approximately 80 degrees centigrade.

45. The apparatus of claim 41, wherein the preset period comprises a value from zero to thirty minutes.

46. The apparatus of claim 30, wherein the active probe further comprises:
   an RF cannula having an insulated tubular body for receiving an RF electrode there through;

a hub at a first end of the tubular body for interfacing with the RF electrode upon its insertion into the tubular body; and a blunt-ended and conductive tubular tip extending from a second end of the insulated tubular body, arcuate approximately along a longitudinal axis of the tubular body and including a conductive spatulate blade having an oval-shaped distal end and conformably attached to a dorsal side of the blunt-ended, conductive and arcuate tubular tip.

47. The apparatus of claim 46, wherein the tubular tip extends from the second end of the tubular body by approximately one centimeter and is curved according to a predetermined radius through an included angle in the range often degrees to thirty degrees.

48. The apparatus of claim 46, wherein the spatulate blade is attached to the tubular tip along a longitudinal center of the spatulate blade.

49. The apparatus of claim 46, wherein the spatulate blade extends laterally from either side of the tubular tip by a first predetermined dimension and longitudinally past a distal end of the tubular tip by a second predetermined distance.

50. The apparatus of claim 46, wherein the spatulate blade conforms to a smooth, oval profile surrounding the end of the tubular tip.

51. The apparatus of claim 46, wherein the tubular tip includes an orifice proximate a distal end of the tubular tip for releasing a liquid substance therefrom.

52. The apparatus of claim 46, wherein the insulated tubular body is configured to receive an RF electrode configured as a thin, conductive wire that extends through the insulated tubular body into conductive contact with the tubular tip.

53. The apparatus of claim 46, wherein the hub includes a locking interface for securing the RF electrode within the insulated tubular body.

54. The apparatus of claim 30, wherein the dispersive probe comprises:

an RF cannula having an insulated tubular body for receiving an RF electrode there through;

a hub at a first end of the tubular body for interfacing with the RF electrode upon its insertion into the tubular body; and a blunt-ended and conductive tubular tip extending from a second end of the insulated tubular body, arcuate approximately along a longitudinal axis of the tubular body and including a conductive spatulate blade having an oval-shaped distal end and conformably attached to a dorsal side of the blunt-ended, conductive and arcuate tubular tip.

55. he apparatus of claim 54, wherein the tubular tip extends from the second end of the tubular body by approximately one centimeter and is curved according to a predetermined radius through an included angle in the range often degrees to thirty degrees.

56. The apparatus of claim 54, wherein the spatulate blade is attached to the tubular tip along a longitudinal center of the spatulate blade.

57. The apparatus of claim 54, wherein the spatulate blade extends laterally from either side of the tubular tip by a first predetermined dimension and longitudinally past a distal end of the tubular tip by a second predetermined distance.

58. The apparatus of claim 54, wherein the spatulate blade conforms to a smooth, oval profile surrounding the end of the tubular tip.

59. The apparatus of claim 54, wherein the tubular tip includes an orifice proximate a distal end of the tubular tip for releasing a liquid substance therefrom.

60. The apparatus of claim 54, wherein the insulated tubular body is configured to receive an RF electrode configured as a thin, conductive wire that extends through the insulated tubular body into conductive contact with the tubular tip.

61. The apparatus of claim 54, wherein the hub includes a locking interface for securing the RF electrode within the insulated tubular body.

* * * * *